(12) United States Patent
Plachta

(10) Patent No.: US 12,414,694 B2
(45) Date of Patent: Sep. 16, 2025

(54) MEDICAL IMPLANT, ASSEMBLY FOR IMPLANTING THE MEDICAL IMPLANT AND ASSEMBLY FOR DETECTING AN INTRACORPOREAL MOVEMENT PATTERN WITH THE MEDICAL IMPLANT

(71) Applicant: Neuroloop GmbH, Freiburg (DE)

(72) Inventor: Dennis Plachta, Vörstetten (DE)

(73) Assignee: NEUROLOOP GMBH, Freiburg (DE)

( * ) Notice: Subject to any disclaimer, the term of this patent is extended or adjusted under 35 U.S.C. 154(b) by 1027 days.

(21) Appl. No.: 17/252,150

(22) PCT Filed: Jun. 13, 2019

(86) PCT No.: PCT/EP2019/065441
§ 371 (c)(1),
(2) Date: Dec. 14, 2020

(87) PCT Pub. No.: WO2019/238803
PCT Pub. Date: Dec. 19, 2019

(65) Prior Publication Data
US 2021/0161381 A1    Jun. 3, 2021

(30) Foreign Application Priority Data
Jun. 13, 2018 (DE) ............... 10 2018 209 449.7

(51) Int. Cl.
*A61B 5/00* (2006.01)
*A61B 5/0215* (2006.01)
(Continued)

(52) U.S. Cl.
CPC .............. *A61B 5/0028* (2013.01); *A61B 5/07* (2013.01); *G06K 7/10366* (2013.01);
(Continued)

(58) Field of Classification Search
CPC ......... A61B 5/0028; A61B 5/07; A61B 90/98; A61B 2562/164; A61B 5/00–7495;
(Continued)

(56) References Cited

U.S. PATENT DOCUMENTS

| 5,241,964 | A | 9/1993 | Mcquilkin |
| 5,921,933 | A | 7/1999 | Sarkis et al. |

(Continued)

FOREIGN PATENT DOCUMENTS

| DE | 19829544 C1 | 1/2000 |
| DE | 69907475 T2 | 2/2004 |

(Continued)

OTHER PUBLICATIONS

Tohmyoh, Hironori, and Sakamoto, Yuhei, Acoustic study of a linear low-density polyethylene film after modification of the crystalline structure by heating, Feb. 20, 2014, Review of Scientific Instruments, 85, 024902 (2014) (Year: 2014).*

(Continued)

*Primary Examiner* — Tse W Chen
*Assistant Examiner* — Evelyn Grace Park
(74) *Attorney, Agent, or Firm* — Fitch, Even, Tabin & Flannery LLP

(57) ABSTRACT

A medical implant with a structure made of at least one biocompatible material, converted from a first spatially compact state into a second spatially deployed and flexible deformable state, has a modulus of elasticity corresponding to the wall of a blood vessel in an order of magnitude between 105 Nm² and 107 N m², has at least one region with an acoustic impedance of more than 1.63·106 kg/m² s, and in the second state has an effective operating surface that is flexibly deformable and at least partially reflects ultrasonic waves. Ultrasonic waves are generated by a sonographic device and which strike an effective operating surface of the (Continued)

intracorporeally applied medical implant and are partially reflected for detecting changes in the spatial distance between the operating surface and the sonography device.

22 Claims, 1 Drawing Sheet

(51) Int. Cl.
*A61B 5/07* (2006.01)
*A61B 90/98* (2016.01)
*G06K 7/10* (2006.01)
*G06K 19/07* (2006.01)
*H01Q 15/14* (2006.01)

(52) U.S. Cl.
CPC ........ *G06K 19/0723* (2013.01); *A61B 5/0215* (2013.01); *A61B 90/98* (2016.02); *A61B 2562/164* (2013.01); *H01Q 15/14* (2013.01)

(58) Field of Classification Search
CPC ........... G06K 7/10366; G06K 19/0723; H01Q 15/14; A61L 2400/12
See application file for complete search history.

(56) References Cited

U.S. PATENT DOCUMENTS

| | | | |
|---|---|---|---|
| 2016/0029998 A1* | 2/2016 | Brister | A61B 8/0833 |
| | | | 600/424 |
| 2019/0022428 A1* | 1/2019 | Maharbiz | A61B 8/48 |

FOREIGN PATENT DOCUMENTS

| | | |
|---|---|---|
| DE | 10 2018 209 449 A1 | 12/2019 |
| WO | 2006/122750 A1 | 11/2006 |
| WO | 2018/024868 A1 | 2/2018 |

OTHER PUBLICATIONS

International Search Report for PCT/EP2019/065441, mailed Sep. 20, 2019; English translation submitted herewith (6 pgs.).

Dennis Plachta, "Baroloop—selective vagal stimulation to treat hypertension" Abstracts—BM1MedPhys 2017—Dresden, Sep. 10-13 • DOI 10.1515/bmt-2017-5048 Biomed. Eng.—Biomed. Tech. 2017; 62(sl): S256-S260 • © by Walter de Gruyter •Berlin• Boston.

\* cited by examiner

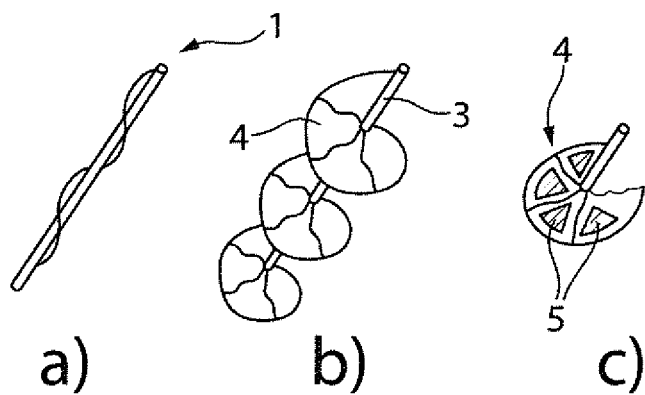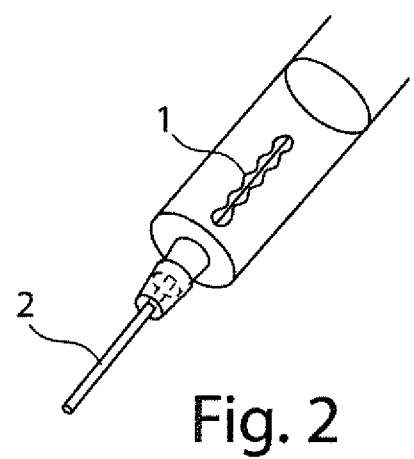
Fig. 1
Fig. 2
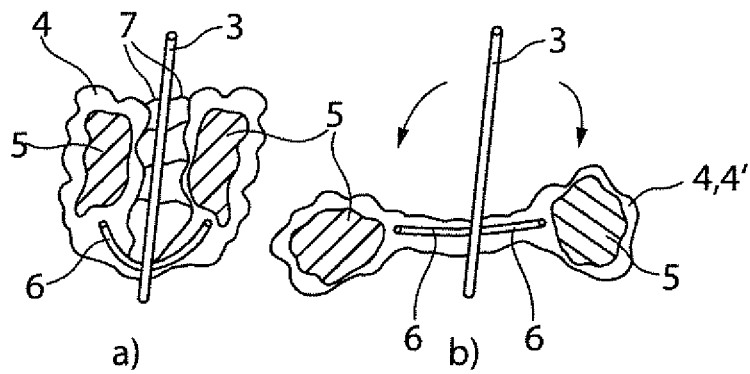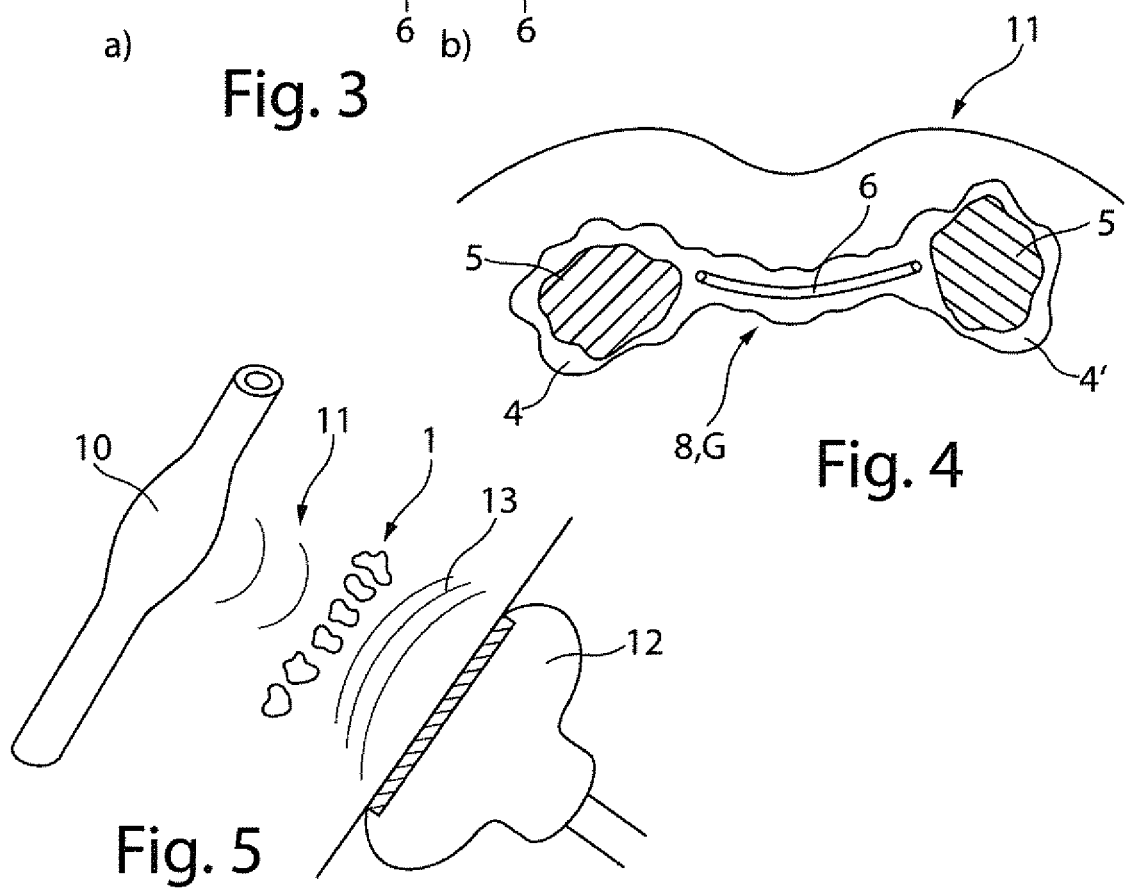
Fig. 3
Fig. 4
Fig. 5

MEDICAL IMPLANT, ASSEMBLY FOR IMPLANTING THE MEDICAL IMPLANT AND ASSEMBLY FOR DETECTING AN INTRACORPOREAL MOVEMENT PATTERN WITH THE MEDICAL IMPLANT

CROSS-REFERENCE TO RELATED APPLICATIONS

This application is a U.S. national phase application filed under 35 U.S.C. § 371 of International Application No. PCT/EP2019/065441, filed Jun. 13, 2019, designating the United States, which claims priority from German Patent Application No. 10 2018 209 449.7, filed Jun. 13, 2018, which are hereby incorporated herein by reference in their entirety.

BACKGROUND OF THE INVENTION

Field of the Invention

The invention relates to a medical implant with a structure which is made of at least one biocompatible material, an assembly for implanting the medical implant, and an assembly for detecting an intracorporeal movement pattern with the medical implant. More particularly, the aim is to detect at least one physiological parameter, preferably the human or animal blood pressure, by use of the medical implant.

Description of the Prior Art

The metrological detection of physiological parameters is usual and commonly practiced in medical technology. An example of such detection of a physiological parameter is the continuous measurement of arterial blood pressure. A device of this type and corresponding detection method, which without the known inflatable arm cuff manages with the pressure sensor functioning in accordance with the Riva-Rocci principle, are, for example, described in U.S. Pat. No. 5,241,964. Here, two non-invasive ultrasonic Doppler sensors are applied extracorporeally via a larger artery. The blood flow signals measured therewith are then used to parametrically characterize a simplified mathematical empirical model of the artery. The determined so-called resonance frequency of the model correlates with the blood pressure. A conventional cuff measurement calibrates the system at irregular intervals to the blood pressure.

DE 198 29 544 C1 also describes an assembly for non-invasive blood pressure measurement. By use of ultrasound or laser Doppler technology, a parameter linked to the blood flow or blood flow rate is measured. For example signal processing downstream of measurement recording includes filtering in order to remove artefacts and other interfering factors.

On the one hand, problematic for recording blood pressure by use of optical or ultrasound-based pulse wave sensors as precisely as possible, is the sensitivity with regard to correct spatial extracorporeal application and orientation of the relevant sensors relative to the blood-conveying vascular regions. Even slight losses of adjustment in the sensor orientation relative to a blood vessel can make it impossible to reliably record the blood pressure. On the other hand, the detectable signal levels, which are of relevance for recording blood pressure, are only very low and therefore require laborious amplification, filtering and signal evaluation. Costly system-related work is required for this.

SUMMARY OF THE INVENTION

The invention largely eliminates the aforementioned drawbacks in the detection of medically relevant physiological parameters, such as, in particular, in the measurement of the blood pressure of a person or an animal through the transcutaneous transmission of ultrasonic waves as well as the detection of intracorporeally reflected ultrasonic wave portions. Firstly, the robustness of the measurement to be carried out against loss of alignment of the components required for emitting and receiving ultrasonic waves must be significantly improved, and secondly, measures must be taken to reduce the metrological complexity and as well as the effort associated with signal evaluation.

An assembly of the invention, which relates to a medical implant which can be applied intracorporeally by use of the assembly detects an intracorporeal movement pattern using the medical implant, through which it is possible to record medically relevant physiological parameters.

The basis of the invention relates to a structure, made of biocompatible material, which, preferably, by use of a cannula assembly, is intracorporeally implantable in a transcutaneous manner, preferably in the immediate vicinity of a blood vessel, and which within the body is able to expand by itself and, if necessary, through the application of external force or energy fields, or through fluid mechanical support, in such a way that the structure forms an "effective operating surface" on which the ultrasonic waves are reflected. The structure made of biocompatible material also has an inherent elasticity, which is comparable with the inherent elasticity of organ vascular walls, in particular that of the wall of the blood vessel relative to which the implanted structure is arranged. Through the choice of material of the biocompatible structure as well as its geometric shape and intracorporeal positioning with regard to a blood vessel, the biocompatible structure, and, in particular, its effective operating surface, undergoes spatial deformations which are caused by natural pulse waves, which in turn are transmitted, through the pulsatile blood pressure in the blood vessel and the vascular wall expanding and contracting in a pulsatile manner, into parts of the body that are directly adjacent to the vascular wall. Through the macroscopically selected size of the effective operating surface, the latter is able to reflect a considerable portion of the ultrasonic waves subcutaneously transmitted by use of an extracorporeally positioned sonographic device. Through this, the requirements relating to precise spatial positioning of the sonographic device relative to the blood vessel are considerably reduced in contrast to the known methods which require direct recording of the blood vessel. In addition, the ultrasonic waves reflected on the effective operating surface create ultrasonic signals with a much higher signal level in the sonographic device, through which the S/N ratio is improved and the amount of subsequent signal processing and evaluation work can be reduced.

The medical implant according to the invention, with a structure made of at least one biocompatible material, is therefore characterized by the combination of the following features: The structure made of biocompatible material can be converted from a first spatially compact state into a second spatially deployed, flexibly deformable state in which the deployed structure has an effective operating surface which is flexibly deformable and can at least partially reflect ultrasonic waves. The biocompatible material of the structure has a modulus of elasticity that corresponds to that of a blood vessel and is in an order of magnitude of between $10^5$ Nm$^2$ and $10^7$ Nm$^2$. Additionally, at least in one region the structure has an acoustic impedance of more than $1.63 \times 10^6$ kg/m² s wherein s is seconds. In the second state, in which the structure made of biocompatible material assumes a spatially deployed shape, the structure has an effective operating surface which is flexibly deformable and can at least partially reflect ultrasonic waves.

Preferably the structure is configured in the form of a film, a mesh, a sponge or tangled structure and due to its materially elastic properties assumes a ball or capsule-shaped spatial form in the first state, which allows introduction and passing through by use of a medical hollow cannula which has a cannula size of between 10 G and 30 G, preferably 17 G and 25 G. Therefore the structure which is compacted in the first state has a diametrical dimension corresponding to the internal diameter of the hollow cannula. In an appropriate manner, in the first state the structure assumes an elongated, ellipsoidal or cylindrical spatial shape in which the cylinder diameter corresponds to the inner diameter of the respectively selected hollow cannula and in this form can be distally pushed or moved through the hollow cannula by use of a stylet or a means on which pressure can be exerted. Instead of using a stylet, it is possible to proximally apply a pressurised fluid, such as a saline solution, to the hollow cannula in order to convey the compacted structure within the hollow cannula through the distal opening.

Preferably the structure expands by itself from its compacted or compressed first state into the second state expanded and enlarged state due to elastic restoring forces inherent in the material. The process of expansion or enlargement into the expanded or unfolded state can be supported by additional external influences. The process of enlargement from the first into the second state takes place within the intracorporeal, moist environment which is able to support the "unfolding process". In a preferred embodiment, the biocompatible material has hygroscopic properties and through the absorption of water is able to effectively support the unfolding or expansion of the structure. Alternatively, or in combination with the measures described above, through the application of an external force or energy field which can be generated by use of an extracorporeal force field generator, an effect is achieved which supports the conversion process from the first into the second state. For this, in a preferred embodiment, the structure made of biocompatible material has at least one means and/or a material property, through which the structure directly or indirectly interacts with the extracorporeally applied force field so that a force moment can be generated that changes at least one of the shape and spatial position of the structure, can support the transformation process from at least one of the first into the second state, and allows positioning of the structure that has been intracorporeally applied and converted into the second state.

The means to be applied to or integrated into the structure must be suitably selected depending on the nature of the force field, for example in the form of a magnetic field, electrical field, acoustic field or a caloric field, that is a temperature field. In the case of a magnetic field, magnetic or magnetizable sections, that are applied in or on the structure, are suitable. In the case of an electrical field, electrically conducting material sections within the structure are used, which interact with an electrodynamic or electrostatic field. In the case of an acoustic force field, devices that are locally applied to the structure and preferably absorb or reflect sound waves are deployed in order to be able to functionally utilize a force moment acting on the structure through sound impulse transmission. Suitable in the case of an extracorporeally applied caloric force field are, for example, bimetallic or bimetallically-acting materials or material combinations which, when integrated into or applied to the structure, can result in local structural deformations.

Conversion materials or "smart materials", for example materials with shape memory, are also suitable for integration into or application on the structure in order to generate deformation forces with the aid of an externally applied force field.

Other suitable materials for implementing an implant according to the invention are, for example, metamaterials or hybrid material combinations of at least one metamaterial, biological tissue material and biocompatible polymers. Also suitable are film-like substrates made of or at least with superficially provided nanostructures, that is in the form of nanotubes or nanograss. Such nano-structures, usually made of carbon or titanium alloys (e.g. Ti6Al4V, TiO2) have specially conditionable physical properties which can be influenced in an appropriate manner in the presence of energy fields.

All materials added to or integrated into the structure, must meet the selection criterion of biocompatibility that is applicable for medical implants.

Typically, the structure is initially present in the second state, that is in a spatially deployed, non-compressed state or in a non-compacted form. Starting from this state, the structure is preferably converted into the first state through at least one of folding, compressing and rolling, and placement in a hollow cannula for implantation.

After corresponding separation of the structure from the hollow cannula, the structure unfolds or expands and forms the effective operating surface on which the ultrasonic waves are reflected. The effective operating surface has a surface area of at least 0.2 mm² and a maximum of 500 mm². In the implanted state, the effective operating surface, which is preferably planar, in one piece and continuous, is orientated relative to a blood vessel so that the pulse waves coming from the blood vessels are transmitted through the effective operating surface as orthogonally as possible, that is the direction of propagation of the pulse waves preferably forms an angle $\alpha$ of 90°±30° with the effective operating surface. In this way the effective operating surface of the implanted structure is dynamically deformed as a function of the pulse waves.

If diagnostic ultrasonic waves, which are transmitted via the skin, that is subcutaneously, by use of a known sonography device, strike the effective operating surface, at least one portion of the ultrasonic waves striking the effective operating surface is reflected and received by the sonography device. The ultrasonic waves received by the sonography device contain information about the respective state of deformation of the effective operating surface of the implanted structure which changes over time and is correlated with the blood pressure prevailing in the blood vessel. In the context of measurement calibration, carried out, for example, using a known inflatable arm cuff with a pressure sensor operating in accordance with the Riva-Rocci principle, the ultrasonic signals received by use of the sonography device can be assigned to quantitative blood pressure values.

In contrast to an aforementioned planar, film-like substrate, in a further preferred form, the structure made of biocompatible material is in the form of a mesh, a sponge or a tangled structure, which in the spatially expanded second state has an effective operating surface that is in projection along a spatial direction, ideally coinciding with the direction of propagation of the ultrasonic waves, on the expanded structure in the second state. For example, in the case of a spherical tangled structure, the effective operating surface is a circular area with a diameter that corresponds to the diameter of the spatial tangled structure.

Advantageously, however, the effective operating surface is not necessarily structured and is preferably formed in an undulating or zig-zag manner, wherein the predetermined structuring remains essentially intact despite the deformation caused by the pulse waves and thereby imprints the ultrasonic waves reflected on the effective operating surface with a typical signature, through which largely fault-free signal detection is made possible and fault signal portions arising from possible intracorporeal interfering reflexes and, which do not have a characteristic signature of this type, can be recognised and invalidated when evaluating the signal.

In order to ensure that in the second state after appropriate unfolding and spatial positioning, the implanted structure remains in situ largely unchanged and does not begin to rove around, a preferred example of embodiment envisages at least one anchoring element on the structure which can anchor itself mechanically in immediately surrounding tissue. For example, the anchoring element is formed into a barb-shaped section directly or indirectly on the structure.

Another preferred embodiment has additional material areas on the structure which reflect electromagnetic waves, preferably in the form of radar waves. Through this, the function of the structure as a pure ultrasonic wave reflector is supplemented by a further function which is based on the interaction with electromagnetic waves.

In combination with or alternatively to the aforementioned advantageous forms of embodiment, the structure has at least one structural area with at least one of an RFID, interdigital electrode and electrical coil structure, via which electrical energy as well as signal-based information can be transmitted in a contactless manner between the implanted structure and an extracorporeal transmitting and receiving unit.

In a further preferred embodiment, the implantable structure also serves as a support for at least one functional material which can be applied to or integrated into the structure made of biocompatible material. The functional material is preferably a pharmaceutical active substance, which in the implanted state of the structure, can be locally released, preferably in accordance with a determined dosing pattern. The release of the active substance can be predefined by at least one of time and individually influenced by use of extracorporeally applicable force fields.

Alternatively, or in combination with a pharmaceutical active substance, in a further embodiment, a biocompatible adhesive acts as a functional substance to immobilize the structure and permanently position it at a particular intracorporeal point with a defined, predetermined spatial position. The biocompatible adhesive is applied to the structure so that in the spatially expanded state of the structure, the adhesive superficially comes into contact with adjacent tissue surfaces, on which a durable joint connection is formed.

As has already been mentioned, hygroscopic material acts as a functional substance introduced into the structure made of biocompatible material as a way of supporting unfolding or expansion through the absorption of tissue fluid.

To implant the medical implant, a hollow cannula is used, which is adapted and designed to be suitable for the subcutaneous implantation of the medical implant in such a way that the structure, present in the first state, can be introduced into or accommodated within the hollow cannula, in order to then distally apply it intracorporeally through the skin from the hollow cannula. Preferably, a pushing device configured as a stylet is used, with which the structure positioned within the hollow cannula can be distally precisely pushed out of the hollow cannula and positioned by an operator. As an alternative to the use of a stylet, a pressurisable fluid reservoir can be connected proximally to the hollow cannula, by which a biocompatible fluid, for example a saline solution, conveys the structure placed in the hollow cannula in the distal direction under the effect of pressure, in order to ultimately apply it intracorporeally. The quantity of fluid additionally releasable intracorporeally in a dosed manner via the hollow cannular, can support the intracorporeal unfolding or expansion of the compressed structure and is then resorbed by the surrounding tissue.

If the structure in an aforementioned, preferred embodiment has a device that can interact with an externally or extracorporeally applied force field, an extracorporeally arranged generator is required, which can generate a force field of the following type: magnetic field, electrical field, caloric field and acoustic field. Preferably the generator is able to generate the force field variably in relation to at least one of the field strength and spatial field distribution.

The medical implant designed in accordance with the invention is a partial component of an assembly for detecting an intracorporeal movement pattern, which also envisages sonographic device, which is known per se, that is positioned extracorporeally in such a way that the ultrasonic waves generated by the sonographic device strike the effective operating surface of the intracorporeally applied medical implant and are at least partially reflected thereon. By detecting the ultrasonic waves reflected on the effective operating surface, changes in the space between the effective operating surface and the sonography device can be recorded which can be used to determine an intracorporeal movement pattern. In particular, in this way, after appropriate calibration of the measurements obtained with the sonography device, it is possible to record the blood pressure and metrologically monitor its change over time. The assembly according to the invention thus makes long-term recording and monitoring of the blood pressure possible without any additional components which have an unpleasant effect on the patients, for example arm pressure cuffs.

Advantageously, the assembly for detecting the intracorporeal movement pattern also could be an extracorporeally arranged transmitter and receiver for an electromagnetic field, the electromagnetic field of which interacts with at least one of an RFID, an interdigital electrode and an electrical coil structure applied on the implanted structure.

BRIEF DESCRIPTION OF THE DRAWINGS

As an example, the invention will be described below, without restricting the general inventive concept, by way of examples of embodiment with reference to the drawings:

FIG. 1a, b, and c show a structure made of biocompatible material for a medical implant;

FIG. 2 shows an assembly for implanting the medical implant;

FIG. 3a, and b show variants of embodiments for unfolding the medical implant;

FIG. 4 shows a medical implant with integrated fluid channels; and

FIG. 5 shows an assembly for detecting an intracorporeal movement pattern

DETAILED DESCRIPTION OF THE INVENTION

FIG. 1a shows a medical implant 1 in a spatially compressed spatial form which is suitable for applying the medical implant 1 by way of a hollow cannula 2 as shown in FIG. 2, for the purpose of intracorporeal positioning. FIG. 2 shows a pointed device for introducing the medical implant 1 by way of a cannula 2 into a human or animal body (not shown). The introduction of the medical implant 1 can take place using a carrier fluid, for example, saline, or in dry form. As part of the implantation procedure, the hollow cannula 2 should be orientated close to a large, arterial blood vessel, as parallel as possible to this vessel, for the purpose of injecting the implant 1 according to the invention.

As shown in FIG. 1*a*, the compressed medical implant 1 comprises a support rod 3, preferably in the form of a polysaccharide rod, along which a planar, film-like structure 4 can be applied which can be configured in one part or in several parts. By retracting the cannula 2 and pushing out the medical implant 1, the planar, film-like structure 4 unfolds radially in a fan-like manner from the support rod 3 in accordance with FIG. 1*b*.

The planar, film-like structure 4 of the medical implant 1 preferably comprises a flexible polymer film, on the surface of which a coating 5 of ultrasound-reflecting material is applied. The ultrasound-reflecting material can also have additional electromagnetic wave-reflecting properties. Preferably nanostructure material in the form of nanotubes or nanograss, for example in the form of carbon nanotubes or titanium oxide nanograss, is suitable for this, see also FIG. 1*c*.

For improved unfolding of the planar medical implant 1 from the compressed stated into the unfolded state, an embodiment illustrated in FIG. 3*a*, *b* illustrates a film-like structure 4 of the medical implant 1 which is interspersed with at least one fluid channel 6, preferably an oil channel. The preferred oil-filled channel 6 generates a mechanical pre-tensioning, which is held in the compressed form of the medical implant 1 with additional threads 7, which connect the planar, film-like structures 4 of the medical implant 1 with the support rod 3, as shown in FIG. 3*a*. As soon as the medical implant 1 is located within the body, the holding threads 7 are resorbed, so that the fluid channels 6 are able to unfold the planar substrate of the medical implant 1, as shown in FIG. 3*b*.

The planar substrate 4 of the medical implant 1 can comprise individual surface areas 4', which are all, or in pairs, connected with a fluid channel 6. In this way it is possible for the individual surface areas 4' to expand in a skewed manner independently of each other which benefits the orientation of the surface areas in the form of reflector surfaces and ultimately the reflected signal. Through a preferred filling of the channels 6, preferably with oil, disruptive influences on the ultrasonic wave reflection behavior of the medical implant 1 can be avoided, particularly as oil is acoustically transparent to ultrasound.

In addition, it can be assumed that through the intracorporeally moist environment, on the basis of an osmotic pressure effect on the medical implant 1, water can penetrate into and through the polymer-based surface substrate 4 of the medical implant 1, so that water enters into the channels 6 thereby increasing the tensioning force of the surface structure of the medical implant 1.

It is also desirable that the individual surface areas 4' of the medical implant 1 vary at least one of their spatial orientation and shape as a function of the intracorporeally occurring pulse waves 11. The spatial variation can be supported and brought about in that the individual surfaces areas 4' of the medical implant 1 are arranged movably with regard to each other. This is ensured through constrictions 8,G between surface areas 4' connected at least in pairs, along which at least one fluid channel 6 runs in each case, as shown in FIG. 4. The constrictions 8,G act in the form of a "natural joint", which can predetermine the mechanical movability of the individual surface areas 4' relative to each other. In the case of the state shown in FIG. 4, the support rod 3 is already resorbed.

FIG. 5 illustrates an intracorporeal blood vessel 10, from which blood pressure waves 11 emanate and interact with the medical implant 1 according to the invention so that the planar, expanded medical implant 1 is spatially deformed by the pressure waves 11. By use of an extracorporeally arranged ultrasonic head 12, ultrasonic waves 13 are subcutaneously transmitted into the region of the medical implant 1. Through the spatial deformations on the medical implant 1 caused by the blood pressure waves 11, the ultrasonic waves 13 are reflected and modulated on the medical implant 1. This modulation in the reflected ultrasonic waves represents a function of the extent of the deformation or deflection of the medical implant 1 and, in connection therewith, a strength of the blood pressure waves 11, which can be detected and precisely measured.

REFERENCE LIST

1 Medical implant
2 Hollow cannula
3 Support rod
4 Film-like substrate
4' Surface areas of the medical implant
5 Nanostructure
6 Hollow channel
7 Resorbable holding threads
8,G Constriction/Joint
10 Blood vessel
11 Blood pressure waves
12 Ultrasonic coupler
13 Ultrasonic waves

The invention claimed is:

1. A medical implant including at least one biocompatible material which is configured for transcutaneous intracorporal implantation through a hollow cannula into a patient or an animal for measuring vascular pressure, comprising:
    means for unfolding the medical implant after passage through the hollow cannula, wherein the medical implant is configured to unfold from a first spatially compact state within the hollow cannula into a second spatially expanded and flexible deformable state within the patient or animal after discharge from the cannula for measuring the vascular pressure of the patient or animal wherein the means for unfolding comprises the at least one biocompatible material having a modulus of elasticity corresponding to a vascular wall of the patient or animal having a magnitude between $10^5$ $N/m^2$ and $10^7$ $N/m^2$ and at least one region having an acoustic impedance of more than $1.63 \cdot 10^6$ $kg/m^2$ s wherein s is seconds; and
    in the second state the at least one biocompatible material has a flexible operating surface that is deformable and partially reflects ultrasonic waves and in the first state the implant has a diameter corresponding to an inner diameter of the hollow cannula sized between 10 G and 30 G.

2. The medical implant according to claim 1, wherein:
    at least one elastic restoring force is inherent in the means for unfolding the at least one biocompatible material which interacts with a force field produced by at least one of an extracorporeal magnetic, an electrical, a caloric and an acoustic force field which produce a force moment changing at least one of shape and spatial position of the medical implant when implanted.

3. The medical implant according to claim 1, wherein the means for unfolding comprises:
a film, a mesh, a sponge or a tangled structure.

4. The medical implant according to claim 1, wherein:
the implant in the second state has an operating surface area of at least 0.2 mm².

5. The medical implant according to claim 1, wherein:
the implant in the second state has a maximum area of 500 mm².

6. The medical implant according to claim 1, wherein the means for unfolding during folding is subject to at least one of compression and rolling that converts the implant from the second state into the first state.

7. The medical implant according to claim 1, wherein:
the implant comprises an area of the at least one biocompatible material that reflects radar waves.

8. Medical implant according to claim 1, wherein:
the implant comprises at least one area which includes at least one of an RFID, an interdigital electrode and an electrical coil.

9. The medical implant according to claim 2, wherein:
the means for unfolding interacts with the extracorporeal force field and comprises at least one material selected from a magnetic material, a magnetizable material, an electrically conductive material, a bi-metallic material, a thermal material, an electrical transducer material, a magnetic transducer material, and a shape memory material.

10. The medical implant according to claim 1, wherein:
the operating surface comprises a one-piece continuous surface.

11. The medical implant according to claim 3, wherein the implant when implanted projects in a spatial direction and forms at least a partially reflecting operating surface for propagating ultrasonic waves in the spatial direction.

12. The medical implant according to claim 1, wherein:
the flexible operating surface is formed or is formable into an undulating or a zig-zag configuration.

13. The medical implant according to claim 1, comprising:
at least one anchoring element including a barbed section contacting the implant.

14. The medical implant according to claim 1, comprising:
at least one of a pharmaceutical active substance, an adhesive, a hygroscopic material which is applied to the implant or which is integrated into the implant.

15. The medical implant according to claim 1, comprises:
one of metamaterials, hybrid material combinations of metamaterial, a biological tissue material and a biocompatible polymer.

16. The medical implant according to claim 3, comprising:
nanostructures or applied nanostructures.

17. The medical implant according to claim 16, wherein:
the nanostructures comprise nanotubes or nanograss.

18. An assembly for implanting the medical implant according to claim 1, wherein:
the medical implant, while within the hollow cannula, is in the first state and is distally appliable from the hollow cannula during the implantation into the patient or animal and comprises:
means for distally releasing the medical implant from the hollow cannula during the implantation into the patient or animal.

19. An assembly for implantation according to claim 18, comprising:
a generator for producing at least one of a magnetic, an electrical, a caloric and an acoustic force field which interacts with the means for unfolding to cause unfolding of the implant after discharge.

20. The assembly according to claim 19, wherein:
the generator varies the acoustic force field by at least one of field strength and a spatial field distribution.

21. An assembly for detecting an intracorporeal movement pattern with the medical implant according to claim 18, comprising a sonographic device, positioned extracorporeally so that ultrasonic waves which are generated by the sonographic device strike an operating surface of the applied medical implant and are partially reflected therefrom for detecting changes in a spatial distance from the operating surface and the sonography device.

22. An assembly according to claim 20, comprising:
a transmitter and a receiver positioned extracorporeally from the patient or animal which senses an electromagnetic field by use of at least one of an RFID, an interdigital electrode and an electrical coil.

* * * * *